United States Patent [19]
Kinnier Wilson

[11] 3,942,522
[45] Mar. 9, 1976

[54] SURGICAL SPLINTS AND MATERIALS THEREFOR

[75] Inventor: Alexander Bruce Kinnier Wilson, Chesham, England

[73] Assignee: National Research Development Corporation, London, England

[22] Filed: Oct. 11, 1974

[21] Appl. No.: 514,317

[30] Foreign Application Priority Data
Oct. 19, 1973 United Kingdom............... 48910/73

[52] U.S. Cl................................ 128/90; 128/89 R
[51] Int. Cl.² ......................................... A61F 5/04
[58] Field of Search........................... 128/90, 89, 87

[56] References Cited
UNITED STATES PATENTS
2,958,325  11/1960  Claydon et al........................ 128/90
3,176,685  4/1965  Smarook................................. 128/90

FOREIGN PATENTS OR APPLICATIONS
297,608  3/1954  Switzerland...................... 128/89 R

*Primary Examiner*—John D. Yasko
*Attorney, Agent, or Firm*—Cushman, Darby & Cushman

[57] ABSTRACT

A deformable sheet material developed for surgical splints comprises a layer of resilient plastics material and a metal mesh reinforcement disposed in the plastics layer nearer one surface thereof. Both components are bendable, but the relative stiffness of the mesh inhibits the resilience of the plastics so that the sheet will 'hold' in different curved configurations with the mesh innermost. Suitable materials are polyethylene and aluminium, and a cushion layer, suitably of irradiated expanded polyethylene, can be bonded to the one surface adjacent the mesh. Also, the sheet can be perforated.

10 Claims, 1 Drawing Figure

U.S. Patent   March 9, 1976   3,942,522
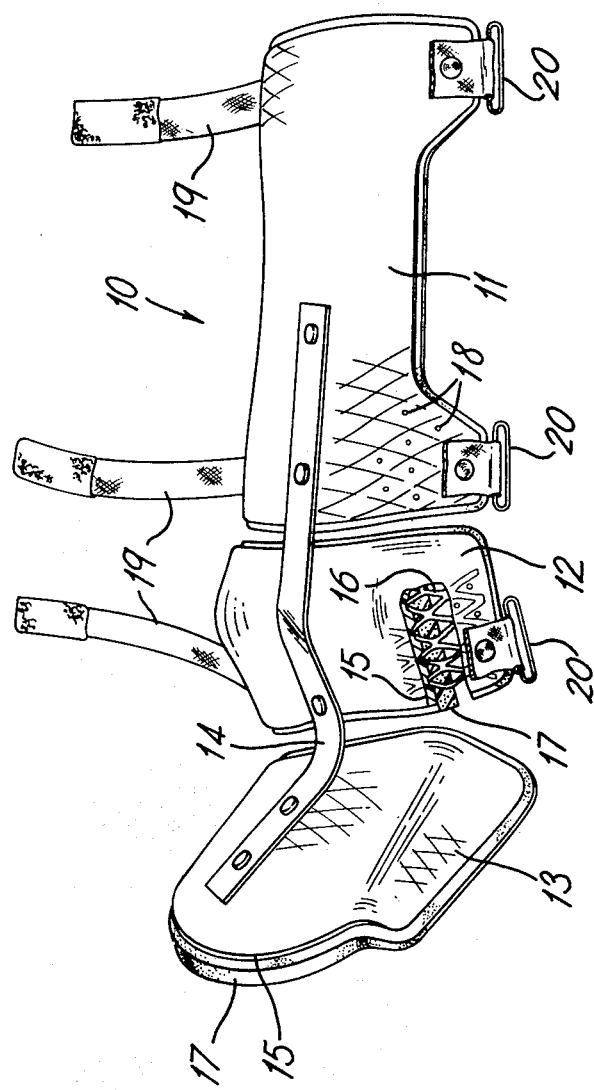

SURGICAL SPLINTS AND MATERIALS THEREFOR

Surgical splints are conventionally made from rigid materials and, as a result, are generally unsuited to various applications in which there is a need for closely fitted support or progressive variation in support geometry during a course of treatment. Such needs are normally met by the use of plaster casts, but this is disadvantageous in being time-consuming and requiring specialist personnel and facilities.

An object of the present invention is to improve this situation and, in one aspect, provides a deformable sheet material forming at least part of, or suitable for use, as a surgical splint, which material comprises a layer of resilient plastics material and a metal mesh reinforcement embedded in said layer nearer one surface thereof, said mesh being bendable but sufficiently stiff to overcome, within limits, the resilience of said plastics material.

Plastics materials suitable for this purpose are best found, for reasons of economy, among those in common use for other purposes, and development of the invention to date has made use of polyethylene, initially of low density form and more recently of high density form. Such materials can, of course, be produced in thin sheet form with great flexibility and little or no resilience. However, a splint requires a certain order of mechanical strength to fulfil its function, while at the same time deformability to suit the human anatomy will require an ability to conform to certain orders of curvature. It has been found that the materials in question need to be of such a thickness for the purposes of mechanical strength, that conformation to the desired curvatures is associated with resilience as a result of the consequent compression of the material on the inside of the curve.

However, the proposed reinforcement is off-set within the plastics material to obviate this difficulty and a splint made from the resultant reinforced material will normally be of an overall curved form defining respectively generally convex and concave major surfaces with the reinforcement nearer the latter surface.

As with the plastics material, the metal mesh is best chosen from those readily available for other purposes, and the present preference is for expanded metal mesh, preferably of aluminium. Expanded metal mesh is normally formed with diamond-shaped interstices and has different strengths in respect of bending along its two diagonal directions which difference can be employed advantageously in a splint. Thus, a splint is commonly employed along a limb and at least partly wrapped circumferentially around the limb, and use of expanded metal reinforcement in this context preferably affords greater strength circumferentially than longitudinally to better stabilise the wrapped geometry. Also, the use of aluminium is preferred for reasons of cost, corrosion resistance relative to other economic metals such as steel, and the possibility of affording coloured finishes by anodising.

The mesh need not be disposed wholly within the plastics material, but it is of course undesirable that there should be any sharp edges of the mesh projecting from the splint. For this last reason, the plastics material preferably extends beyond the mesh in the general plane of the sheet to avoid outer projections of metal, while inner projections can be avoided by use of an additional material within the splint if the mesh is not wholly embedded in the sheet. Such an additional material is desirable in any case for purposes of cushioning and, conveniently, this cushioning material is integrated with the splint, when it can also assist in stabilising the mesh in the plastics material. A suitable material for this purpose is a foamed plastics material and preferably of a kind which is readily bonded with that of the first-mentioned sheet.

Also, it may be desirable, particularly for use in hot climates, for the presently proposed sheet material to be perforated.

For purposes of example only, one embodiment of a splint according to the invention is schematically illustrated in the accompanying drawing.

The illustrated splint is denoted at 10 and comprises three parts 11, 12, 13 made of a material as described more generally above, which parts are interconnected by a metal bar 14. The material of the parts 11, 12, 13 comprises a sheet 15 of low density polyethylene which is bonded with expanded anodised aluminium mesh 16 by heating the sheet 15 and impressing the same into the interstices of the mesh to project therethrough. In addition a cushion layer 17 of expanded polyethylene which has been irradiated is bonded by heat to the projections of sheet 15 through the mesh 16. The splint part 12 is partly cut away in the drawing to clearly illustrate its laminated structure. Also, the parts 11, 12 and 13 may be perforated as indicated by holes 18 passing through the interstices of the mesh 16.

The parts 11, 12, 13 are each formed to an overall curved form having respective generally convex and concave major faces with their respective cushion layers 17 innermost, and their meshes 16 wholly enclosed. The overall form of the parts when connected by the bar 14 follows that of the underside of the forearm, wrist and hand, with the wrist bent back and the fingers forward. More particularly the part 11 has a generally trough or semi-cylindrical shaping which includes four circumferentially extending portions at its corners. These portions have fabric tapes 19 rivetted thereto to serve as straps and carry buckles 20 whereby this part can be secured to the forearm. The part 12 is also of a trough shape, although flatter than part 11 and having a bend formed in the base portion of the trough about a fold line inclined across the trough base. This part also carries two tapes 19 and a buckle 20 and is secured around the heel of the palm produced by the bent wrist. The remaining part 13 is a flat-based trough which serves to support the fingers.

The parts 11, 12, 13 are formed to the shapes just described but are, of course, deformable to suit individual patients, and the relative relationship of the parts is similarly adjustable by bending the bar 14, which in this instance is of soft aluminium rivetted to the parts 11, 12, 13. Equally important is the fact that the form and relative disposition of the part 13 can be progressively adjusted to support the fingers in different dispositions as they heal after surgery, this being the primary function of the illustrated splint.

I claim:

1. A redeformable surgical splint of the type having a concave inner face for placement adjacent to the body of a patient, a convex outer face and a predetermined thickness, said splint comprising a layer of resilient plastics material having a first surface defining said inner face, a bendable metal mesh reinforcement embedded in said layer to extend in said layer adjacent to said inner face, said layer having a second surface defining said outer face which is spaced a greater distance from said bendable metal mesh than said inner face.

2. A sheet material according to claim 1 wherein said mesh has diamond-shaped interstices.

3. A sheet material according to claim 1 wherein said metal is aluminium.

4. A sheet material according to claim 1, wherein said plastics material is polyethylene.

5. A sheet material according to claim 1 comprising a layer of cushion material bonded to said one surface.

6. A sheet material according to claim 5 wherein said cushion material is an expanded plastics material.

7. A sheet material according to claim 5 wherein said cushion material is irradiated expanded polyethylene.

8. A sheet material according to claim 1, which sheet material is perforated.

9. A splint according to claim 1 wherein said configuration is a trough, and said mesh has diamond-shaped interstices with major and minor diagonal directions respectively extending transversely and longitudinally relative to said trough.

10. A surgical splint comprising at least two troughs as recited in claim 9, a deformable metal strip connected to each of said troughs to interconnect the latter in mutually-spaced generally longitudinal sequence, and a strap assembly connected to at least one of said straps to interconnect the opposed longitudinal side portions thereof.

* * * * *